July 19, 1932. H. L. ICKES Plant Pat. 19
DAHLIA
Filed Feb. 18, 1931
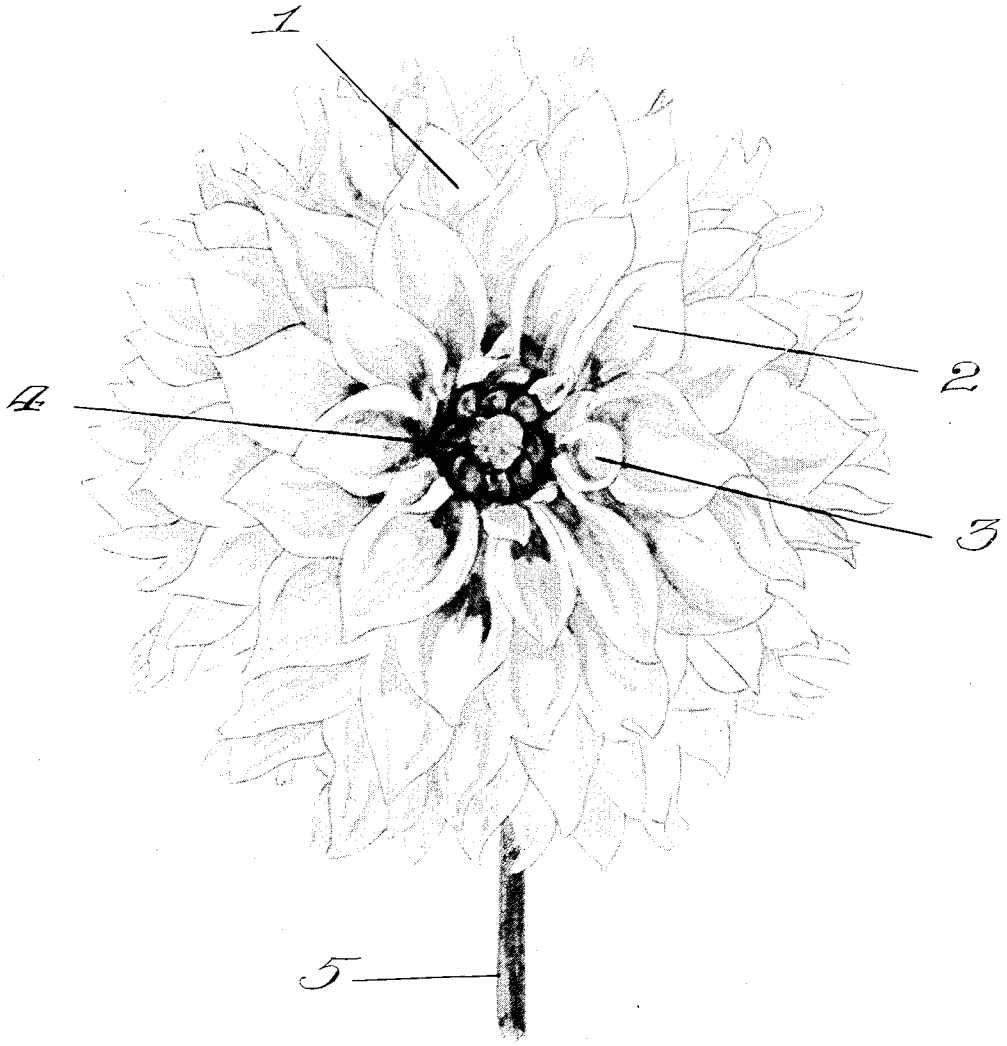
Inventor:
Harold L. Ickes
By Wallace R Lane
Atty.

Patented July 19, 1932

Plant Pat. 19

UNITED STATES PATENT OFFICE

HAROLD L. ICKES, OF HUBBARD WOODS, ILLINOIS

DAHLIA

Application filed February 18, 1931. Serial No. 516,660.

Among the objects of my invention and discovery is to produce a new variety of dahlia having a new, unusual and striking blend of color which is pleasing to the sight and which will not fade either on the bush or as a cut flower.

Another object of my invention is to produce a new variety of dahlia having a long and firmer stem which is important in keeping the large blossoms or flowers from drooping on the bush and also to prevent any breaking off due to the size and weight of the blossom or flower.

Another object of my invention is to produce a new variety of dahlia which has fine sturdy growing habits, with clean foliage, so as to make cultivation of it easier in most climates without expert care and management.

A further object of my invention is to produce a new variety of dahlia which is more floriferous than related varieties and such other objects, advantages and capabilities as will later more fully appear, and as are inherently possessed thereby.

Referring to the drawing—

Fig. 1 is a full front view of my new variety of dahlia in color, showing a small portion of the stem and removed from the bush.

Referring now in more detail to the drawing, every effort has been made to produce the actual coloration of the blossom or flower, but no amount of skill with color can produce the beauty which life produces with this particular coloration. The blossom or flower is a full double dahlia classed as Formal Decorative according to the re-classification of dahlias recommended by the American Dahlia Society.

The ray florets 1 are somewhat regularly arranged. Individually they are somewhat rounded at the outer ends converging to a noticeable but small point at the tip. The outer side margins of these ray florets 1 are very definitely involute with the outer ray florets tending also to curve back. The outer ray florets are light coral red while those ray florets 2 approaching the center have definite coloration of Eugenia red. These colors are described with reference to A. Mearz and M. Rea Pauls, A Dictionary of Color, McGraw-Hill Publishing Company, 1930, Coral red being 2 I.10 and Eugenia red 3 K.2.

Further, the reverse side of these ray florets 1 and 2 are considerably lighter in color and have a slightly golden glint. The central ray florets 3 are somewhat cupped. The center 4 is composed of small yellow green ray florets which form a rather firm center. A small portion of this firm center 4 may sometimes be seen when the blossom or flower is in full bloom.

The stem 5, only a portion of which is shown, is a brownish hunter's green in color and very firm to the touch. The stem 5 is very stout but slender and straight. Large blossoms or flowers are borne and held erect well above the foilage. The stem is unusually long for dahlias.

To produce my new dahlia I adopt the following procedure although it is to be understood that any other suitable methods may be used. I first select a fine specimen of the well known variety of dahlia "Jersey's Beauty" which is classed as a Formal Decorative and is generally spoken of as Eosine pink in color, as the pollen bearer. As the development of this selected blossom or flower is nearing full maturity, I select a fine specimen of the well known variety of dahlia "Mrs. I. de Ver Warner" which is classed as Formal Decorative and which is Cattleya rose or Mauve pink in color, on the bush, being careful to select a blossom which can be kept free from ants and insects. When the yellow pollen dust on the Jersey's Beauty is dry and shiftable, it is taken and with the aid of a piece of cotton on the end of a small stick, it is placed in the center of the blossom selected to ripen into seed. After the blossom or flower has been hand fertilized it is kept free from ants and insects. When the flower dies all the petals are removed and the pod is allowed to dry and turn brownish in color. Caution must be exercised not to permit the pod to become too dry. The pod is then cut and the seeds removed. The seeds are then dried and packed away until spring.

These seeds are used to develop seedlings which produce plants which come to full maturity in one season. From seedlings produced by such a crossing as I have described herein I invented and discovered my new variety of dahlia.

Although one of the chief charms of this new dahlia lies in its distinctive color combination, it possesses many other characteristics which are important. The blossom or flower is large and bold and of good form, the usual size of the blossom or flower being from six to nine inches in diameter and three to five inches in depth. The foliage is dark green in color, with a leathery texture and is free from insect attack. The plant or bush has a compact, sturdy and healthy growth and is a medium to large grower. Another important characteristic is that it is more floriferous than related varieties. Without disbudding, from eight to twelve perfect blooms or flowers grow on a single bush, all with the long, straight firm stems. By the usual methods disbudding very much larger blossoms or flowers may be produced for display or show purposes.

To reproduce asexually this new variety I employed the usual methods in dahlia culture which are division of the roots with a portion of the stalk and cuttings from shoots developed on the roots and stalks.

Having thus fully described my invention, I claim:

The dahlia as herein shown and described characterized by its color being Coral red, shading to Eugenia red towards the center, involute florets and strong healthy growing habits.

In witness whereof, I hereunto subscribe my name to this specification.

HAROLD L. ICKES.